United States Patent
Shim et al.

(10) Patent No.: US 9,931,265 B2
(45) Date of Patent: Apr. 3, 2018

(54) WALK-ASSISTIVE APPARATUS AND METHOD OF CONTROLLING THE WALK-ASSISTIVE APPARATUS

(71) Applicant: Samsung Electronics Co., Ltd., Suwon-si, Gyeonggi-do (KR)

(72) Inventors: Young Bo Shim, Seoul (KR); Young Do Kwon, Yongin-si (KR); Kyung Shik Roh, Seongnam-si (KR)

(73) Assignee: Samsung Electronics Co., Ltd., Gyeonggi-do (RE)

( * ) Notice: Subject to any disclaimer, the term of this patent is extended or adjusted under 35 U.S.C. 154(b) by 462 days.

(21) Appl. No.: 14/599,767

(22) Filed: Jan. 19, 2015

(65) Prior Publication Data
US 2015/0231018 A1 Aug. 20, 2015

(30) Foreign Application Priority Data

Feb. 18, 2014 (KR) .................. 10-2014-0018504

(51) Int. Cl.
*A61H 1/00* (2006.01)
*A61H 3/00* (2006.01)
(Continued)

(52) U.S. Cl.
CPC .............. *A61H 3/00* (2013.01); *A61F 2/68* (2013.01); *A61H 1/024* (2013.01); *A61H 1/0244* (2013.01);
(Continued)

(58) Field of Classification Search
CPC ........ A61H 1/02; A61H 1/0237; A61H 1/024; A61H 1/0244; A61H 1/2251;
(Continued)

(56) References Cited

U.S. PATENT DOCUMENTS

| 2,489,291 | A | * | 11/1949 | Henschke | ............... | A61F 2/604 623/41 |
| 4,442,390 | A | * | 4/1984 | Davis | .................. | G05D 3/1472 318/660 |
| 5,020,790 | A | * | 6/1991 | Beard | ................... | A61F 5/0102 482/4 |
| 6,409,693 | B1 | * | 6/2002 | Brannigan | ............ | A61F 5/0123 128/882 |

(Continued)

FOREIGN PATENT DOCUMENTS

| JP | 2003181789 A | 7/2003 |
| JP | 2007330299 A | 12/2007 |

(Continued)

*Primary Examiner* — Steven Douglas
(74) *Attorney, Agent, or Firm* — Harness, Dickey & Pierce, P.L.C.

(57) ABSTRACT

A walk-assistive apparatus may include at least one joint that corresponds to at least one joint of a wearer, at least one link that connects the joint, and is rotated in response to rotation of the joint, a spring that is mounted in the link or the joint so that a length of the spring is changed in accordance with rotation of the link or the joint, and a processor that controls the change in the length of the spring to compensate for a weight by gravity when the wearer walks. Accordingly, the walk-assistive apparatus and a method of controlling the walk-assistive apparatus may use a mechanical element such as a spring to reduce energy, and weight compensation having uniform performance may be performed even in an arbitrary posture.

19 Claims, 12 Drawing Sheets

(51) Int. Cl.
*A61F 2/68* (2006.01)
*A61H 1/02* (2006.01)

(52) U.S. Cl.
CPC ............... *A61H 2201/0192* (2013.01); *A61H 2201/1215* (2013.01); *A61H 2201/1246* (2013.01); *A61H 2201/164* (2013.01); *A61H 2201/165* (2013.01); *A61H 2201/1628* (2013.01); *A61H 2201/5061* (2013.01); *A61H 2201/5069* (2013.01); *A61H 2201/5084* (2013.01)

(58) Field of Classification Search
CPC .... A61H 2001/2248; A61H 2001/2251; A61H 3/00; A61H 3/0277; A61H 2003/007; A61H 2003/0283; A61H 2201/0157; A61H 2201/12; A61H 2201/16; A61H 2201/1628; A61H 2201/164; A61H 2201/1642; A61H 2201/1657; A61H 2201/1666; A61H 2201/1673; A61H 2201/1676; A61H 2201/5007; A61H 2201/5058; A61H 2201/5061; A61H 2205/10; A61H 2205/106; A61H 2205/108

See application file for complete search history.

(56) References Cited

U.S. PATENT DOCUMENTS

| | | | |
|---|---|---|---|
| 7,544,155 B2 * | 6/2009 | Agrawal | B25J 9/0006 482/69 |
| 7,883,546 B2 * | 2/2011 | Kazerooni | A61F 2/68 623/27 |
| 8,500,823 B2 * | 8/2013 | Herr | A61F 2/64 623/24 |
| 2010/0185301 A1 * | 7/2010 | Hansen | A61F 2/6607 623/47 |
| 2010/0243344 A1 | 9/2010 | Wyrobek et al. | |
| 2011/0040216 A1 | 2/2011 | Herr et al. | |
| 2011/0251534 A1 * | 10/2011 | Matsuoka | A61H 1/024 601/35 |
| 2013/0226048 A1 * | 8/2013 | Unluhisarcikli | A61H 3/00 601/34 |
| 2016/0113831 A1 * | 4/2016 | Hollander | A61H 1/0244 623/31 |

FOREIGN PATENT DOCUMENTS

| | | |
|---|---|---|
| JP | 2008253639 A | 10/2008 |
| JP | 2011217825 A | 11/2011 |
| KR | 1996-0008259 | 6/1996 |

* cited by examiner

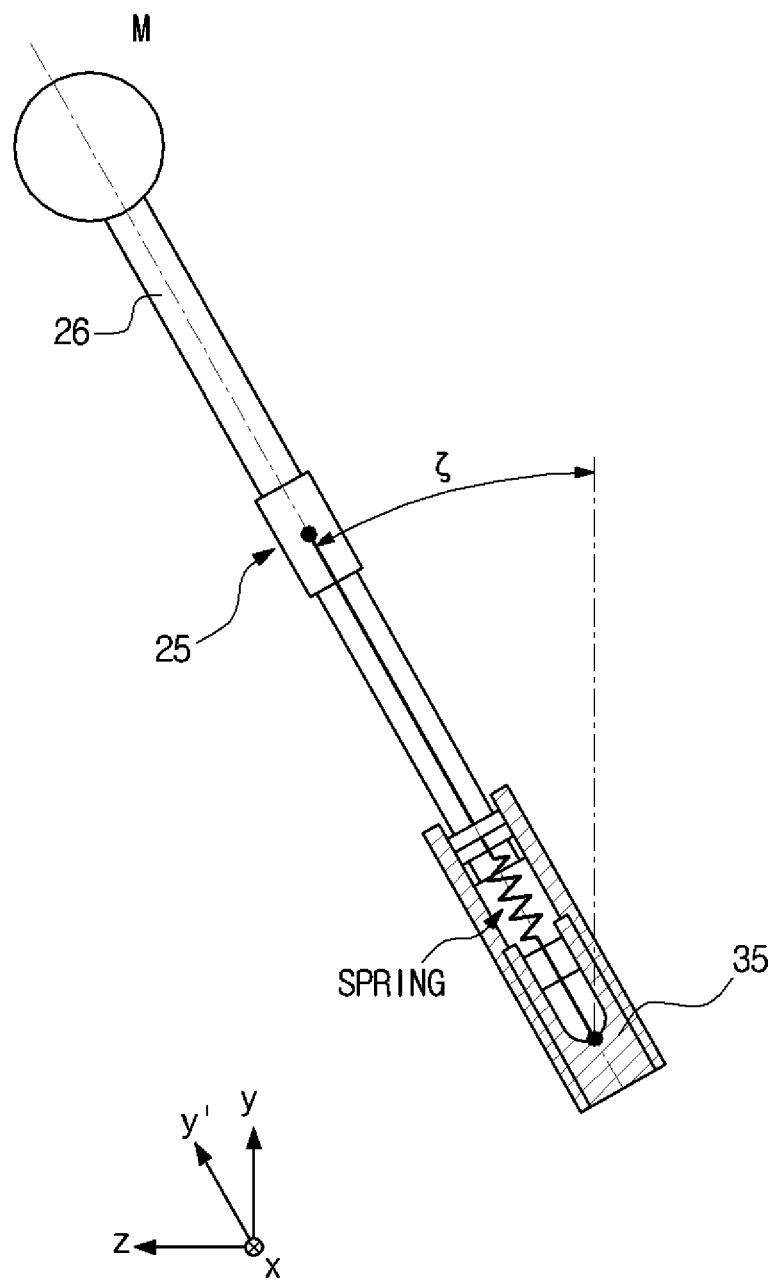

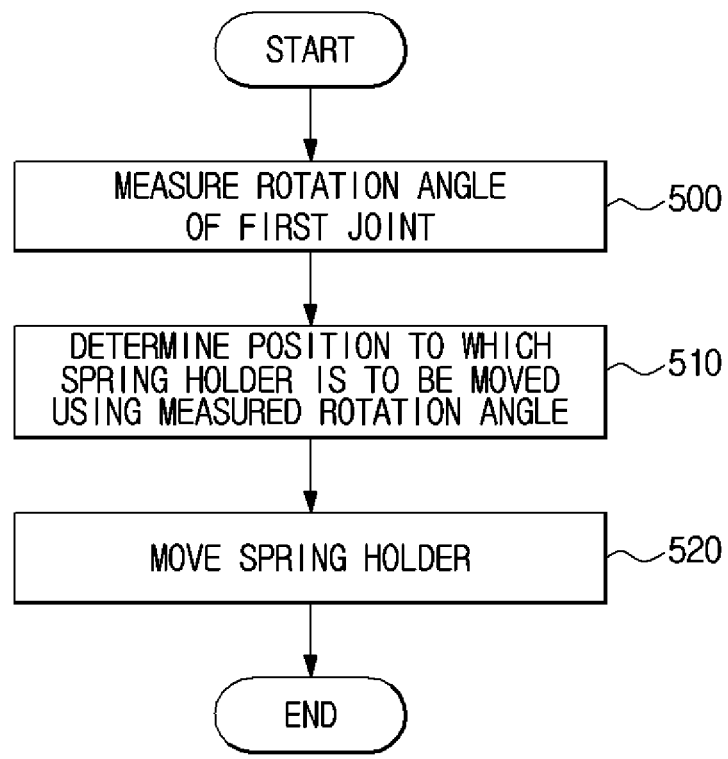

WALK-ASSISTIVE APPARATUS AND METHOD OF CONTROLLING THE WALK-ASSISTIVE APPARATUS

CROSS-REFERENCE TO RELATED APPLICATION

This application claims the benefit of Korean Patent Application No. 10-2014-0018504, filed on Feb. 18, 2014 in the Korean Intellectual Property Office, the entire disclosure of which is incorporated herein by reference.

BACKGROUND

1. Field

Example embodiments relate to a walk-assistive apparatus and a method of controlling the walk-assistive apparatus.

2. Description of the Related Art

A walk-assistive apparatus is a mechanism that may assist a wearer with a disability affecting their ability to walk so that the wearer can more easily walk. Walking may become uncomfortable for people due to innate reasons such as genetic defects or acquired reasons such as age, diseases, accidents, and the like, and walk-assistive apparatuses may relieve such discomfort in walking.

As such a walk-assistive apparatus, a walk-assistive car in which at least one wheel and a support are installed, a walk-assistive robot that assists a wearer with walking by applying a force required for walking to muscles of the human body, or the like may be used.

The walk-assistive robot may be fixed to the buttocks, the femoral region, the shanks, and the like of the human body, and assist movements of muscles and joints by applying a force such as a rotational force by an actuator or various other mechanical means. The wearer may walk more easily with the assistance of the walk-assistive robot.

SUMMARY

Example embodiments are related to a walk-assistive apparatus and a method of controlling the walk-assistive apparatus. In at least some example embodiments, the walk-assistive apparatus may be configured to compensate for weight using a spring.

Additional aspects of the example embodiments will be set forth in part in the description which follows and, in part, will be obvious from the description, or may be learned by practice of the example embodiments.

In accordance with some example embodiments, the walk-assistive apparatus may include at least one joint that corresponds to at least one joint of a wearer; at least one link that connects the joint, and is rotated in response to rotation of the joint; a spring that is mounted in the link or the joint so that a length of the spring is changed in accordance with rotation of the link or the joint; and a processor that controls the change in the length of the spring to compensate for a weight by gravity when the wearer walks.

The joint may include a first joint and a second joint respectively corresponding to a hip joint and a knee joint of the wearer, and the link may include a first link that connects the first joint and the second joint and is rotated in response to rotation of the first joint.

Also, the joint may include a fourth joint that is provided around the second joint and rotated independently from the second joint.

Also, the walk-assistive apparatus may further include a reference bar that is fixed to the fourth joint to form a reference axis of the rotation of the fourth joint.

Also, the walk-assistive apparatus may further include a spring that is fixed at one end thereof to the fourth joint, and fixed at the other end thereof to a spring holder movably provided on the first link.

Also, the processor may control movement of the spring holder.

Also, the processor may determine a movement position of the spring holder, and controls the spring holder to be moved to the determined position.

Also, the first joint may be rotated in a front, rear, left, or right direction of the wearer in response to movement of the hip joint when the wearer walks.

Also, the fourth joint may be rotated to allow the reference bar to be maintained in a parallel state with a gravity direction.

Also, the walk-assistive apparatus may further include at least one string that connects the first joint and the fourth joint.

Also, a length of the at least one string wound around the first joint and the fourth joint may be adjusted so that the parallel state is maintained when the fourth joint is rotated.

Also, an intermediate end of the spring may be fixed to the reference bar.

Also, the processor may determine a movement position $P_2$ of the spring holder using the Equation: $P_2 = P_1 \cdot \cos(\zeta)$, where $$P_1 = \frac{Mgl}{K \cdot u},$$

$\zeta$ denotes an angle at which the first joint is rotated to the left or right of the wearer in the gravity direction as a center axis, $P_1$ denotes a position from a center of the second joint to the spring holder at an initial $\zeta=0$, M denotes a weight of the wearer including a weight of the walk-assistive apparatus, g denotes the acceleration of gravity, l denotes a length of the first link, K denotes a spring constant, and u denotes a distance between a position of the spring fixed to the reference bar and the center of the second joint.

Also, the walk-assistive apparatus may further include a worm gear, wherein the processor controls the movement of the spring holder by driving the worm gear.

Also, the walk-assistive apparatus may further include a position adjuster that is rotated in accordance with driving of the worm gear to move the spring holder.

Also, the spring holder may include a slot, and the position adjuster may include a protrusion that is inserted into the slot.

Also, the protrusion may be moved inside the slot to move the spring holder when the position adjuster is rotated in accordance with the driving of the worm gear.

Also, the processor may determine a rotation angle α of the position adjuster using the Equation:

$$\alpha = \cos^{-1}\left(\frac{P_2 - C}{R}\right) = \cos^{-1}\left(\frac{P_1 \cdot \cos(\zeta) - C}{R}\right),$$

and control the driving of the worm gear so that the position adjuster is rotated by the determined angle α, where ζ denotes an angle at which the first joint is rotated to the left or right of the wearer in the gravity direction as a central axis, $P_2$ denotes a determined movement position of the spring holder, $P_1$ denotes a position to the spring holder from the center of the second joint at an initial $\zeta=0$, C denotes a distance from the center of the second joint to a rotation center of the position adjuster, and R denotes a distance from a rotation center of the position adjuster to a center of the protrusion.

In other example embodiments, the method of controlling a walk-assistive apparatus may include rotating a first joint in a front, rear, left, or right direction of a wearer in response to movement of a hip joint of the wearer when the wearer walks; measuring a rotation angle of the first joint; determining a movement position of a spring holder from a second joint corresponding to a knee joint of the wearer based on the measured angle; and moving the spring holder to correspond to the determined position on a first link connecting the first joint and the second joint.

The rotating of the first joint may include rotating a fourth joint provided around the second joint and rotated independently from the second joint, in response to the rotation of the first joint.

Also, the rotating of the first joint may include rotating the fourth joint so that a reference bar fixed to the fourth joint is maintained in a parallel state with a gravity direction.

Also, the rotating of the first joint may include adjusting a length of at least one string wound around the first joint and the fourth joint, the at least one string connecting the first joint and the fourth joint, so that the parallel state is maintained.

Also, the moving of the spring holder may include changing a length of a spring that is fixed at one end thereof to the fourth joint, and fixed at the other end thereof to the spring holder.

Also, the moving of the spring holder may include changing a length from an intermediate end of the spring fixed to the reference bar to the other end of the spring fixed to the spring holder.

Also, the determining of the movement position of the spring holder may include determining the movement position $P_2$ of the spring holder using the Equation: $P_2 = P_1 \cdot \cos(\zeta)$, where $$P_1 = \frac{Mgl}{K \cdot u},$$

$\zeta$ denotes an angle at which the first joint is rotated to the left or right of the wearer in the gravity direction as a center axis, $P_1$ denotes a position from a center of the second joint to the spring holder at an initial $\zeta=0$, M denotes a weight of the wearer including a weight of the walk-assistive apparatus, g denotes the acceleration of gravity, l denotes a length of the first link, K denotes a spring constant, and u denotes a distance between a position of the spring fixed to the reference bar and the center of the second joint.

Also, the moving of the spring holder may include controlling the movement of the spring holder by driving a worm gear.

Also, the moving of the spring holder may include moving the spring holder by rotating a position adjuster in accordance with the driving of the worm gear.

Also, the moving of the spring holder may include moving the spring holder by moving a protrusion provided in the position adjuster inside a slot provided in the spring holder when the position adjuster is rotated.

Also, the method of controlling a walk-assistive apparatus may further include determining a rotation angle $\alpha$ of the position adjuster using the Equation $$\cos^{-1}\left(\frac{P_2 - C}{R}\right) = \cos^{-1}\left(\frac{P_1 \cdot \cos(\zeta) - C}{R}\right),$$

where $\zeta$ denotes an angle at which the first joint is rotated to the left or right of the wearer in the gravity direction as a central axis, $P_2$ denotes a determined movement position of the spring holder, $P_1$ denotes a position to the spring holder from the center of the second joint at an initial $\zeta=0$, C denotes a distance from the center of the second joint to a rotation center of the position adjuster, and R denotes a distance from a rotation center of the position adjuster to a center of the protrusion.

Also, the moving of the spring holder may include controlling driving of the worm gear so that the position adjuster is rotated by the determined angle $\alpha$.

BRIEF DESCRIPTION OF THE DRAWINGS

These and/or other aspects of the example embodiments will become apparent and more readily appreciated from the following description of the embodiments, taken in conjunction with the accompanying drawings of which:

FIGS. 8A and 8B are views showing positioning when rotation is performed on a plane not parallel with a gravity direction;

FIG. 10 is a flowchart showing a method of controlling a walk-assistive apparatus according to some example embodiments.

DETAILED DESCRIPTION

Figure 1:
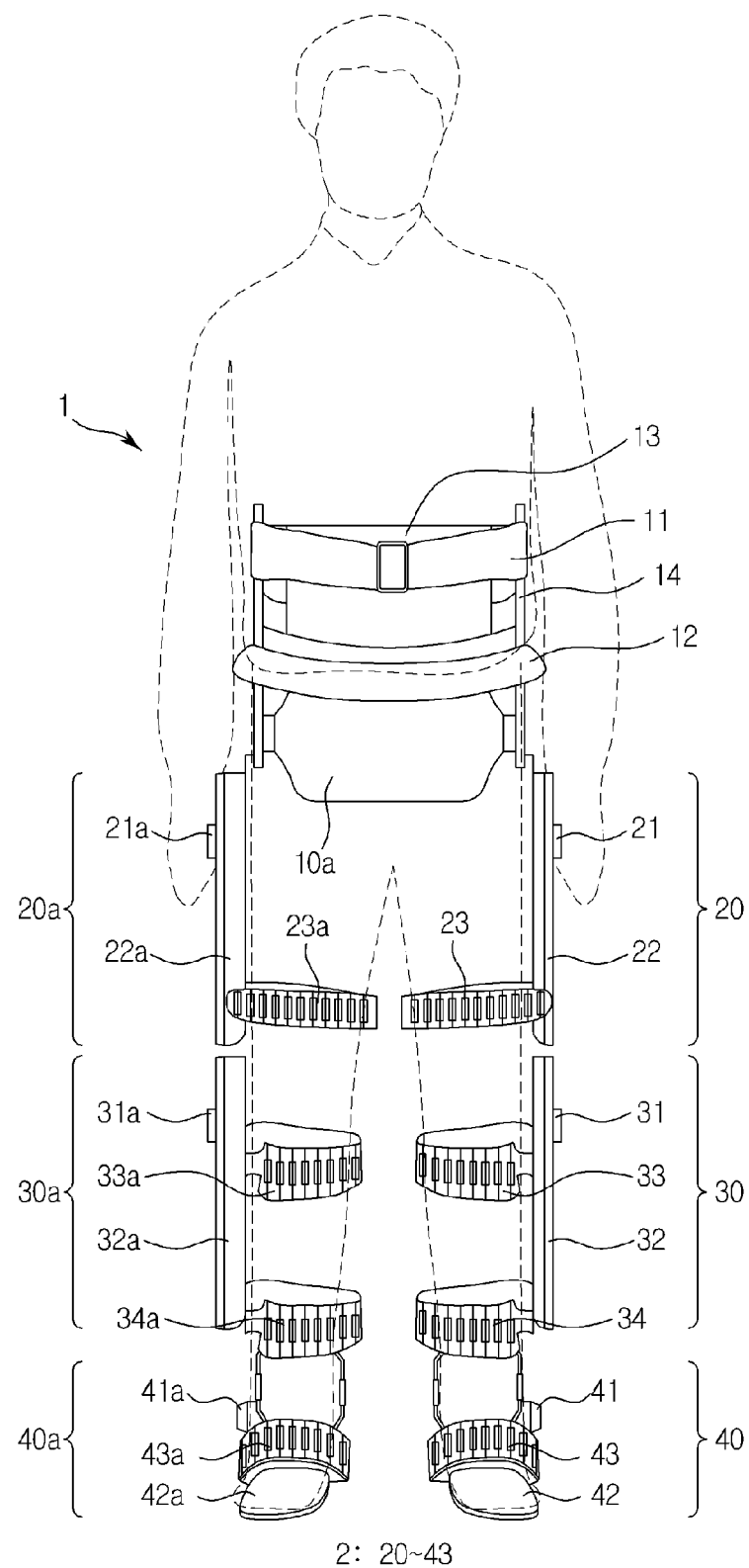
FIG. 1 is a front view showing a walk-assistive apparatus according to some example embodiments.

Reference will now be made in detail to the example embodiments, some examples of which are illustrated in the accompanying drawings, wherein like reference numerals refer to like elements throughout.

Example embodiments will now be described more fully with reference to the accompanying drawings, in which some example embodiments are shown. In the drawings, the thicknesses of layers and regions are exaggerated for clarity. Like reference numerals in the drawings denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
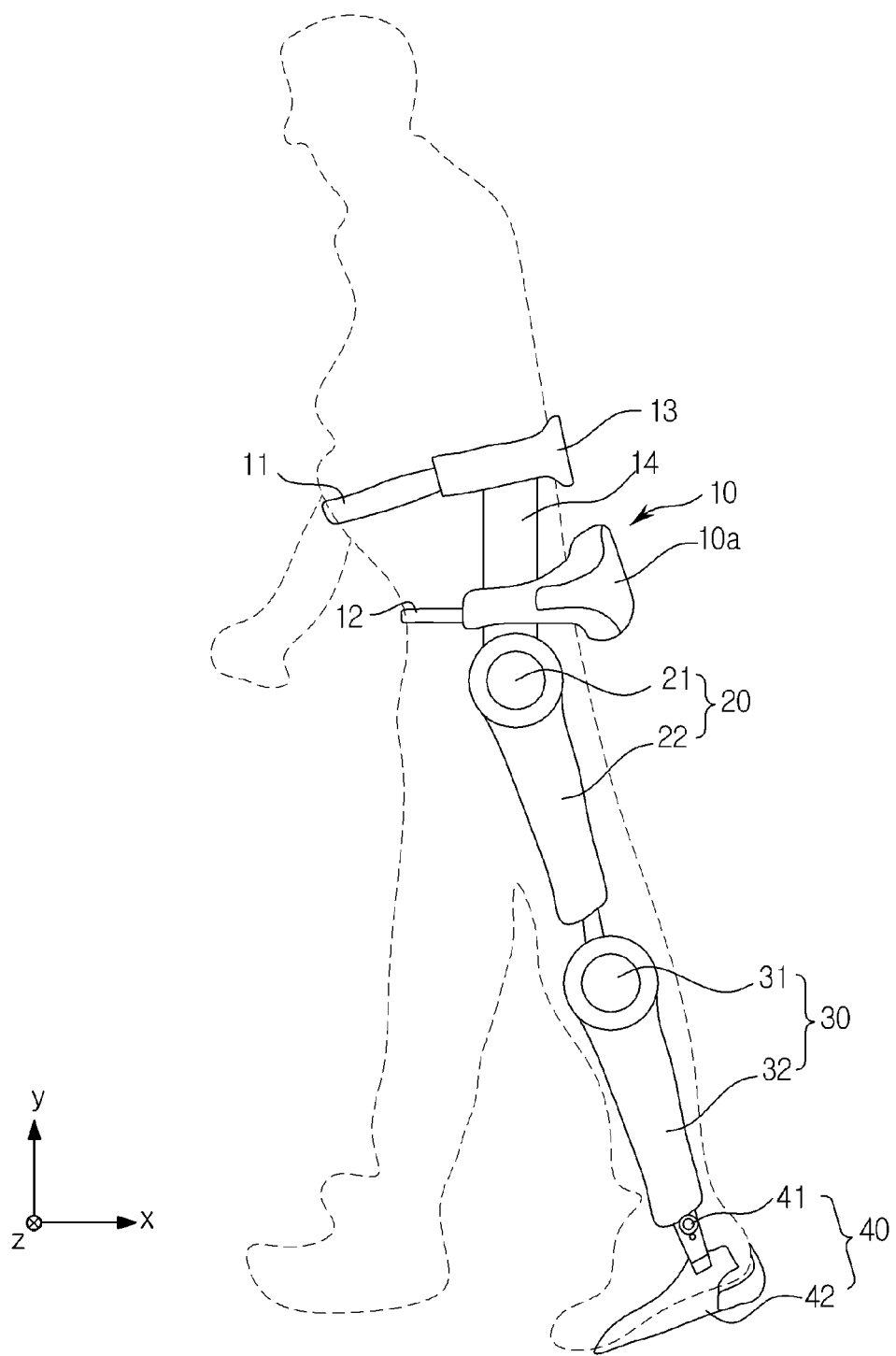
FIG. 2 is a side view showing a walk-assistive apparatus according to some example embodiments.

FIG. 1 is a front view showing a walk-assistive apparatus according to some example embodiments. FIG. 2 is a side view showing a walk-assistive apparatus according to some example embodiments.

As shown in FIGS. 1 and 2, the walk-assistive apparatus 1 may have an exoskeleton structure of a joint system similar to the human body. Further, as discussed below with reference to FIG. 3, the walk-assistive apparatus 1 may include a walk-assistive unit 2 that is worn on the whole or a part of a lower limb of a wearer so as to assist the wearer with walking and a main body 10 that controls the walk-assistive unit 2 or collects a variety of information.

The walk-assistive unit 2 may include at least one of a first structure unit 20, a second structure unit 30, and a third structure unit 40 as shown in FIGS. 1 and 2.

Hereinafter, a case in which the walk-assistive apparatus 1 includes all of the first structure unit 20, the second structure unit 30, and the third structure unit 40 will be described, however, example embodiments are not limited thereto.

Further, the walk-assistive unit 2 may include a single first structure unit 20, a single second structure unit 30, and a single third structure unit 40. In this instance, the first structure unit 20, the second structure unit 30, and the third structure unit 40 may be worn on at least one of the left leg and the right leg of the wearer. Also, as shown in FIG. 1, the walk-assistive unit 2 may include a pair of the first structure units 20 and 20a, a pair of the second structure units 30 and 30a, and a pair of the third structure units 40 and 40a so that the walk-assistive unit 2 can be worn on the left leg and the right leg of the wearer. When the walk-assistive unit 2 includes the pair of first structure units 20, the pair of second structure units 30, and the pair of third structure units 40, functions and operations of the respective structure units 20, 30 and 40 are substantially the same. The walk-assistive unit 2 may include one of some of the plurality of structure units 20, 30 and 40 and pairs of the other structure units. For example, the walk-assistive unit 2 may include one pair of the first structure units 20 and 20a, one second structure unit 30 and one third structure unit 40.

Hereinafter, the single first to third structure units 20, 30 and 40 will be described, but the corresponding descriptions may be equally applied to pairs of the respective structure units.

The first structure unit 20 may assist movements of the femoral region and the hip joint of the wearer when the wearer walks. The first structure unit 20 may include at least one first joint 21 and at least one first link 22.

The first joint 21 is a part corresponding to the hip joint of the human body and is provided in a connection region of a second waist support unit 14 and the first link 22. As discussed below in more detail with reference to FIG. 3, the first joint 21 may receive a torque from a joint driving unit 220 configured to rotate in various directions and angles.

Example embodiments may have at least one degree of freedom (DOF) for rotation of the first joint 21. Here, DOF refers to DOF in forward kinematics or inverse kinematics, and means an independent parameter required for representing a position of an object. For example, an object in a three-dimensional space having x, y, and z axes has three DOFs (that is, a position on each axis) for determining a spatial position of the object and three DOFs for determining a spatial orientation of the object. That is, when it is assumed that an object is movable along each axis and rotatable with respect to each axis, it can be understood that the object has six DOFs.

The first link 22 serves to support the femoral region of the wearer. The first link 22 may be formed in various shapes, as necessary, and, for example, may have a bar shape as shown in FIGS. 1 and 2. A length of the first link 22 may be adjustable. Thus, the wearer may adjust the length of the first link 22 to match the length of his or her own femoral region before or while wearing the walk-assistive apparatus 1.

An end of the first link 22 is connected to the first joint 21 to be rotated in accordance with rotation of the first joint 21. A range of the rotation of the first joint 21 may be within an operation range of the hip joint of the wearer. Also, a first fixing unit 23 for fixing the first link 22 to the femoral region of the wearer may be provided in an inner side or an outer side of the first link 22. Thus, when the first link 22 is rotated, the femoral region of the wearer fixed to the first link 22 by the first fixing unit 23 may be rotated in the same direction as the first link 22.

For example, as the first joint 21 is rotated in front and rear directions of the wearer, the first link 22 is rotated by drawing a circular arc on a plane (hereinafter referred to as an "x-y plane") formed by the x and y axes with respect to the first joint 21. In addition, the femoral region of the wearer may be rotated on the x-y plane with respect to the first joint 21 in the same direction as the rotation direction of the first link 22. As another example, as the first joint 21 is rotated in left and right directions of the wearer, the first link 22 is rotated by drawing a circular arc on a plane (hereinafter referred to as a "y-z plane") formed by the y and z axes with respect to the first joint 21. In addition, the femoral region of the wearer may be rotated on the y-z plane with respect to the first joint 21 in the same direction as the rotation direction of the first link 22.

In other words, the first joint 21 and the first link 22 are rotated by the torque applied from the joint driving unit 220, and therefore the wearer may be assisted by assist power provided from the walk-assistive apparatus 1 when walking or raising his or her leg.

Meanwhile, the first fixing unit 23 may be made of a metal material, an elastic material such as rubber and the like. The first fixing unit 23 may be implemented in the form of a chain as shown in FIG. 1, in the form of a band with elasticity, or in the form of a strap, however example embodiments are not limited thereto. For example, various fixing means which can be considered by those skilled in the art in order to fix the first link 22 to the femoral region or the like may be included in an example of the first fixing unit 23.

The second structure unit 30 may assist movements of the lower thigh region and the knee joint of the wearer when the wearer walks. The second structure unit 30 may include at least one second joint 31 and at least one second link 32.

The second joint 31 is a part corresponding to the knee joint of the human body, and is provided in a connection region of the first link 22 and the second link 32. As discussed below in more detail with reference to FIG. 3, the second joint 31 may receive a torque from the joint driving unit 220 that is configured to rotate in various directions and angles, and may have at least one DOF.

The second link 32 serves to support the lower thigh region of the wearer. The second link 32 may be formed into various shapes, as necessary, and may have the same bar shape as the first link 22 as shown in FIGS. 1 and 2. However, a thickness and a size of the second link 32 may be different from those of the first link 22, and may be formed into a different shape, as necessary. Also, a length of the second link 32 may be adjustable in the same manner as the first link 22. Thus, the wearer may adjust the length of the first link 22 to match his or her own lower thigh region before or while wearing the walk-assistive apparatus 1.

An end of the second link 32 is connected to the second joint 31 to be rotated along rotation of the second joint 31, and at least one second fixing unit 33 and 34 for fixing the second link 32 to the lower thigh region of the wearer may be provided in an inner side or an outer side of the second link 32. Thus, when the second link 32 is rotated, the lower thigh region of the wearer fixed to the second link 32 by the second fixing units 33 and 34 may be rotated in the same direction as the second link 32.

For example, as the second joint 31 is rotated in front and rear directions of the wearer, the second link 32 is rotated with respect to the second joint 31 by drawing a circular arc on the x-y plane. In addition, the lower thigh region of the wearer may be rotated on the x-y plane with respect to the second joint 31 in the same direction as the rotation direction of the second link 32. As another example, as the second joint is rotated in left and right directions of the wearer, the second link 32 is rotated with respect to the second joint 31 by drawing a circular arc on the y plane. In addition, the lower thigh region of the wearer may be rotated on the y-z plane with respect to the second joint 31 in the same direction as the rotation direction of the second link 32.

In other words, the second joint 31 and the second link 32 may be rotated by the torque applied from the joint driving unit 220, and such a structure of the second structure unit 30 assists movements of the lower thigh region and the knee joint of the wearer. Thus, the wearer may be assisted by assist power provided from the walk-assistive apparatus 1 when walking or raising his or her leg.

Meanwhile, configurations, structures, materials, and the like of the second fixing units 33 and 34 may be the same as those of the first fixing unit 23.

The third structure unit 40 may assist operations of ankles of the wearer when the wearer walks. The third structure unit 40 may include at least one third joint 41 and a foot rest unit 42.

The third joint 41 is a part corresponding to the ankle joint of the human body, and is provided in the connection region of the second link 32 and the foot rest unit 42. The third joint 41 may also receive a torque from the joint driving unit 220 configured to rotate in various directions and angles, and may have one DOF.

The foot rest unit 42 is a part for supporting soles of the wearer, and includes a third fixing unit 43 to mutually fix the foot of the wearer seated on the foot rest unit 42 and the foot rest unit 42. The configuration, the structure, the material, and the like of the third fixing unit 43 may be the same as those of the first fixing unit 23 or the second fixing units 33 and 34.

The main body 10 may control operations of the walk-assistive apparatus 1 or acquire information related to the walking. In addition, the main body 10 supports an upper body of the wearer to assist the wearer in stably wearing the walk-assistive apparatus 1.

The main body 10 may include at least one of a housing 10a and an input unit.

In the housing 10a, a printed circuit board in which various processing devices such as a central processing unit (CPU), a graphic processing unit (GPU), and the like and a semiconductor chip can be installed, and various kinds of storage devices may also be in the housing 10a, as necessary.

As discussed in more detail below in regard to FIG. 3, in the housing 10a, a processor 120 may be provided to generate control signals for controlling the walk-assistive unit 2. In addition, the generated control signals may be transmitted to the walk-assistive unit 2 through wired or wireless communication.

The housing 10a may stably fix various components while safely protecting the various components.

In the main body 10, an input unit (not shown) capable of inputting a variety of information for operations of the walk-assistive apparatus 1 or operating various devices may be provided, thereby providing a user interface (UI).

The main body 10 may further include a first waist support unit 13, a second waist support unit 14, a first waist fixing unit 11, and a second waist fixing unit 12.

The first waist support unit 13 and the second waist support unit 14 serve to support the waist of the wearer. For this, an end of the second waist support unit 14 is connected to the first joint 21, and other end thereof is connected to the first waist support unit 13. The first waist support unit 13 may be designed as a curved flat plate to conform to a waist shape.

The first waist fixing unit 11 may fix the first waist support unit 13 to the waist of the wearer, and the second waist fixing unit 12 may fix the housing 10*a* to the waist or buttocks of the wearer. The first waist fixing unit 11 and the second waist fixing unit 12 may be made of a metal material or an elastic material such as rubber. The first waist fixing unit 11 and the second waist fixing unit 12 may be provided in the form of a chain, a band with elasticity, or various kinds of straps. Other than these, the first waist fixing unit 11 and the second waist fixing unit 12 may include various fixing means which can be considered by those skilled in the art in order to fix the first waist support unit 13 or the housing 10*a* to the waist, the buttocks, or the like.

Figure 3:
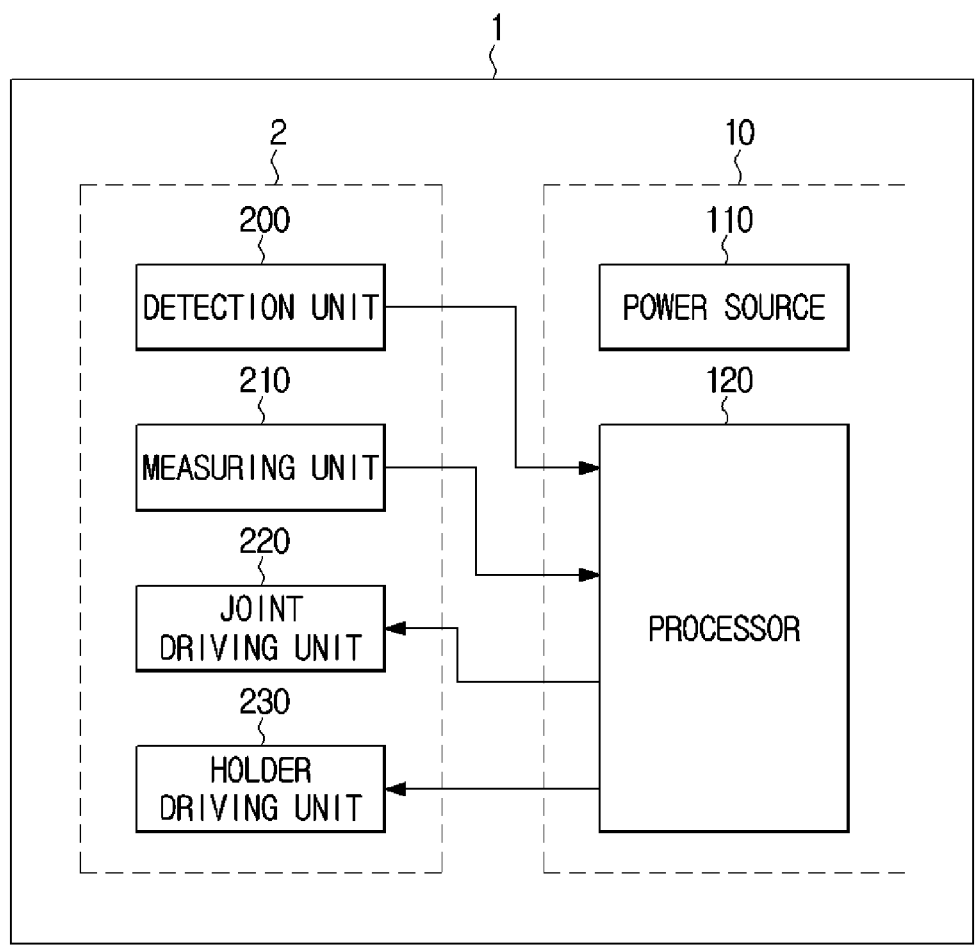
FIG. 3 is a control block diagram showing a walk-assistive apparatus according to some example embodiments.

FIG. 3 is a control block diagram showing a walk-assistive apparatus according to some example embodiments.

The walk-assistive apparatus 1 may include at least one detection unit 200, at least one measuring unit 210, at least one joint driving unit 220, a holder driving unit 230, a power source 110, and the processor 120 to assist the wearer's movements when the wearer walks or lifts or lowers his or her legs.

In some example embodiments, as shown in FIG. 3, the at least one detection unit 200, the at least one measuring unit 210, the at least one joint driving unit 220, and the holder driving unit 230 may be included in the walk-assistive unit 2, and the power source 110 and the processor 120 may be included in the main body 10, however, example embodiments are not limited thereto.

The at least one joint driving unit 220 may include a first joint driving unit 220*a* for driving the first joint 21, a second joint driving unit 220*b* for driving the second joint 31, and a third joint driving unit 220*c* for driving the third joint 41.

The joint driving unit 220 may generate torques having various sizes in accordance with control signals from the processor 120, and apply the generated torques to the respective joints 21, 31, and 41 to enable the respective joints 21, 31, and 41 to be rotated in various directions and angles.

The joint driving unit 220 may be implemented by a motor that generates a torque in accordance with electric energy supplied from the power source 110 of the main body 10 or the like. In this instance, the motor may be a motor including an encoder. In addition, the joint driving unit 220 may be implemented as at least one piston or cylinder device that is operated by the electric energy supplied from the main body 10 or the like or a pressure of a fluid, for example, by pressure such as oil pressure or air pressure to thereby generate a torque. The joint driving unit 220 may be implemented to include at least one motor or include at least one piston and at least one cylinder device.

The at least one detection unit 200 may be divided into a first detection unit 200*a* included in the first structure unit 20, a second detection unit 200*b* included in the second structure unit 30, and a third detection unit 200*c* included in the third structure unit 40. In addition, the at least one measuring unit 210 may also be divided into a first measuring unit 210*a* included in the first structure unit 20, a second measuring unit 210*b* included in the second structure unit 30, a third measuring unit 210*c* included in the third structure unit 40.

The first detection unit 200*a* may detect at least one operation of movements of the first joint 21, the first link 22, and the wearer's hip joint. The first detection unit 200*a* may generate electrical signals in response to the detected movement, thereby acquiring information related to walking. The information related to the walking may include at least one of a joint angle, an inclination of the first link 22, an angular speed of the joint, and an acceleration of the joint. The information obtained in the first detection unit 200*a* may be transmitted to the processor 120.

The first detection unit 200*a* may include at least one of, for example, a joint angle sensor, an inclination sensor, an acceleration sensor, and an inertial measurement unit (IMU). The first detection unit 200*a* may be installed in at least one of the first joint 21 and the first link 22. According to some example embodiments, the first detection unit 200*a* may be installed in both of the first joint 21 and the first link 22. In other example embodiments, a part of the first detection unit 200*a* may be installed in the first joint 21 and the other part may be installed in the first link 22. For example, the joint angle sensor may be installed in the first joint 21, and the inclination sensor or IMU may be installed in the first link 22.

The first measuring unit 210*a* is connected to the first joint 21 to obtain information related to movements of the first joint 21. The information related to the movement of the first joint 21 may include at least one of a rotation angle, an angle speed, and an angle acceleration. The first measuring unit 210*a* may measure a joint angle, a speed, and an acceleration using an encoder value when the first joint driving unit 220*a* is a motor with the encoder. A parameter measured in the first measuring unit 210*a* may be transmitted to the processor 120.

The second detection unit 200*b* may detect at least one of the movements of the second joint 31, the second link 32, and the wearer's knee joint to convert the detected movement to electrical signals, and transmit the electrical signals to the processor 120. The second detection unit 200*b* may include at least one of the joint angle sensor, the inclination sensor, the acceleration sensor, and the IMU. The second detection unit 200*b* may be installed in at least one of the second joint 31 and the second link 32. In the same manner as the first detection unit 200*a*, a part of the second detection unit 200*b* may be installed in the second joint 31, and the other part thereof may be installed in the second link 32.

The second measuring unit 210*b* may obtain information related to the movement of the second joint 31. The information related to the movement of the second joint 31 may include at least one of a rotation angle, an angle speed, and an angle acceleration. When the second joint driving unit 220*b* is a motor with the encoder, the second measuring unit 210*b* may measure a joint angle, a speed, and an acceleration using an encoder value. A parameter measured in the second measuring unit 210*b* may be transmitted to the processor 120.

The third detection unit 200*c* may detect at least one of movements of the third joint 41, the foot rest unit 42, and the wearer's ankle joint. The third detection unit 200*c* may include at least one of a joint angle sensor, an inclination sensor, an acceleration sensor, and an IMU. In some example embodiments, the third detection unit 200*c* may include a pressure sensor. The pressure sensor may be installed in the foot rest unit 42, and may detect whether the wearer wears the walk-assistive apparatus 1 or whether the wearer stands up by detecting the wearer's weight. The pressure sensor may be a ground reaction force sensor that may detect a ground reaction force (GRF) transmitted to the wearer's foot. Signals generated in accordance with detection by the third detection unit 200*c* may be transmitted to the processor 120.

The third measuring unit 210c may measure information related to movements of the third joint 41, and may transmit the measured information to the processor 120. When the third joint driving unit 220c is a motor with the encoder, the third measuring unit 210c may measure a joint angle, a speed, and an angle acceleration using an encoder value.

The power source 110 may supply power to various components within the housing 10a or components such as the respective joints 21, 31, and 41 of the walk-assistive unit 2. The power source 110 may be built in the housing 10a, or separately provided outside the housing 10a.

In addition, the power source 110 may be a primary battery, or a secondary battery. When the power source 110 is a primary battery, the power source 110 may include a mercury battery, a manganese battery, an alkaline battery, a lithium battery, or the like. When the power source 110 is a secondary battery, the power source 110 may include a nickel-cadmium (Ni—Cd) battery, a nickel-metal hydride (Ni—NH) battery, a lead acid battery, a lithium ion (Li-ion) battery, a lithium polymer battery, or the like.

In addition to the processor 120, the main body 10 may also include a memory (not shown).

The processor 120 may be implemented by at least one semiconductor chip disposed on a printed circuit board built in the housing 10a. The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processor 120 as a special purpose computer to perform the operations illustrated in FIG. 10, such that the processor is configured to determine an amount of tension to apply to the second joint 32 to maintain a rotation angle θ between the first joint 21 and the waist of the wearer using a spring such that the spring compensates for a weight of the wearer.

Therefore, the walk-assistive apparatus 1 may compensate for the weight of the wearer to maintain the rotation angle θ of the first joint 21 without applying a separate torque (T) thereto.

The processor 120 may determine operation states of the hip joint, the knee joint, and the ankle joint or states of the joints 21, 31, and 41 corresponding to each joint based on information transmitted from the detection unit 200 and the measuring unit 210. In addition, the processor 120 may generate control signals for controlling the walk-assistive apparatus 1 based on the determined states of the hip joint, the knee joint, and the ankle joint or the joints 21, 31, and 41 corresponding to each joint.

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

Figure 4:
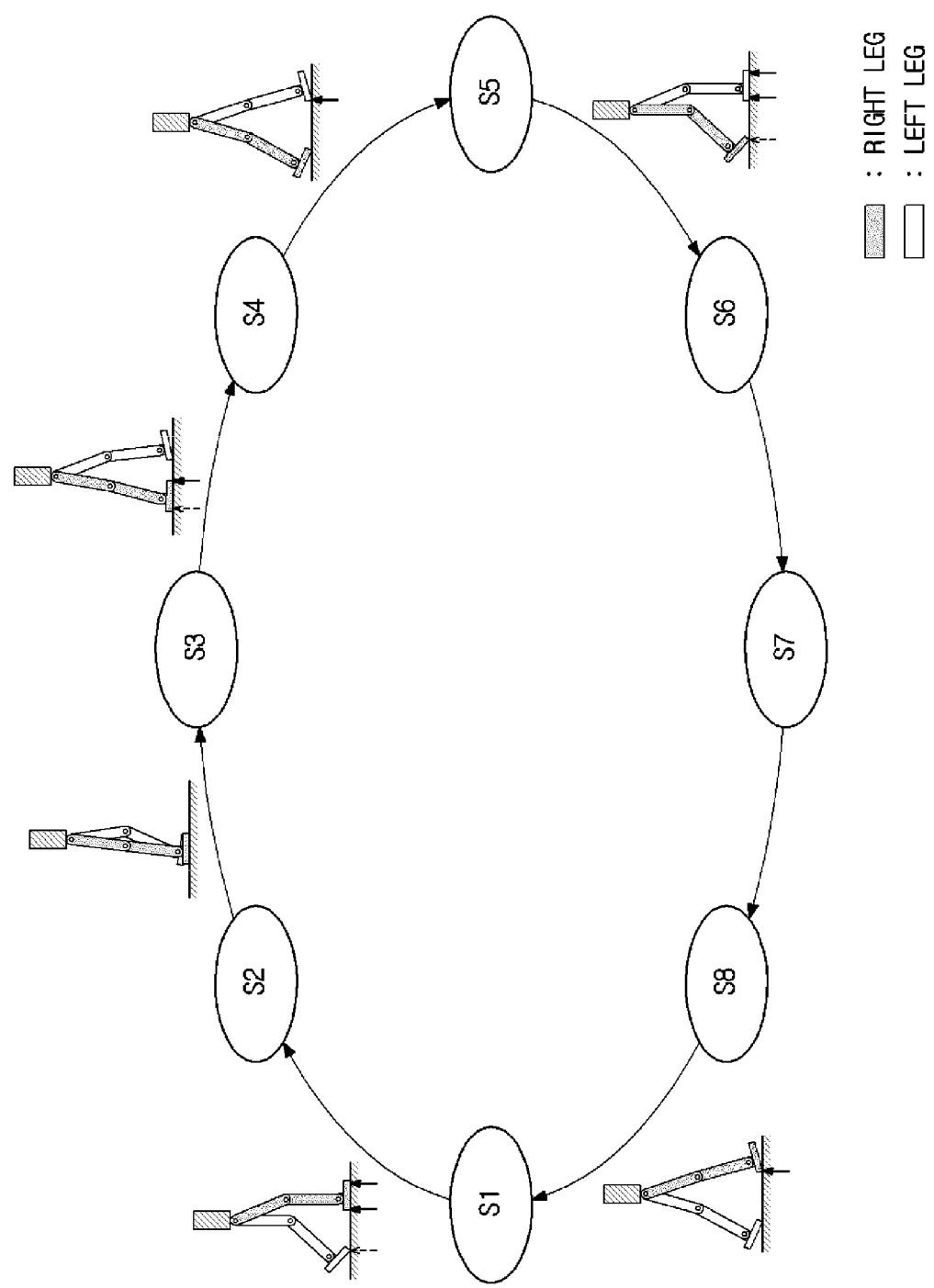
FIGS. 4 and 5 are views showing a finite state machine model as an example of a walking model.
Figure 5:
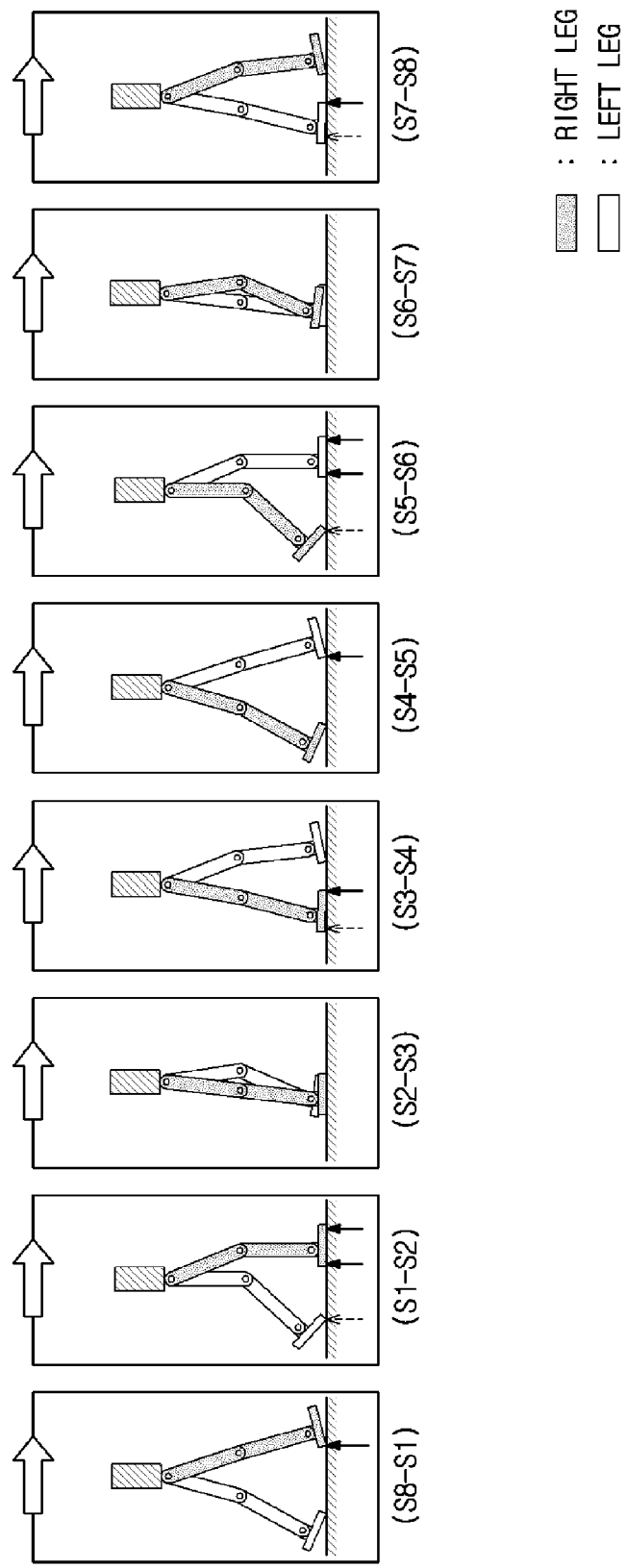

FIGS. 4 and 5 are views showing a finite state machine model as an example of a walking model.

As shown in FIG. 4, walking may be divided into eight stages (s1 to s8).

In the first stage (s1) of walking, the right leg may be in a loading response (LR) state, and the left leg may be in a pre-swing (PSw) state. During transition from the eighth stage (s8) of walking to the first stage (s1) of walking, the heel of the right foot may touch the ground as shown in FIGS. 4 and 5. On the other hand, toes of the left foot may touch the ground and the heel of the left foot may be separated from the ground (s8 to s1).

In the second stage (s2) of walking, the right leg may be in a mid stance (MSt) state, and the left leg is in an initial swing (ISw) state. During transition from the first stage (s1) to the second stage (s2), the toes and heel of the right foot may simultaneously touch the ground, and the left leg may start a swing operation. The heel of the left foot may be first separated from the ground, and the toes of the left foot may be separated from the ground after the heel of the left foot is separated from the ground (s1 to s2).

In the third stage (s3) of walking, the right leg may still be in the mid stance state, and the left leg may be in a mid swing (MSw) state. During transition from the second stage (s2) to the third stage (s3), the toes and heel of the right foot may all touch the ground, and the left leg may continuously perform a swing operation. The right foot and the left foot may be positioned adjacent to each other (s2 to s3).

In the fourth stage (s4) of walking, the right leg may be in a terminal stance (TSt) state, and the left leg may be in a terminal swing (TSw) state. During transition from the third stage (s3) to the fourth stage (s4), the heel of the right foot may start to be separated from the ground. On the other hand, the toes of the right foot may still touch the ground. Meanwhile, the left foot may maintain a state of not touching the ground (s3 to s4).

In the fifth stage (s5) of walking, the left leg may be in the loading response (LR) state and the right leg may be in the pre-swing (PSw) state, opposite to the first stage (s1) of walking.

During transition from the fourth stage (s4) to the fifth stage (s5), the heel of the left foot may touch the ground. Meanwhile, the toes of the right foot may touch the ground and the heel of the right foot may be separated from the ground (s4 to s5).

In the sixth stage (s6) of walking, the left leg may be in the mid stance (MSt) state, and the right leg may be in the initial swing (ISw) state. During transition from the fifth stage (s5) to the sixth stage (s6), the toes and heel of the left foot may simultaneously touch the ground. The right leg may start to perform a swing operation while the toes of the right foot are separated from the ground (s5 to s6).

In the seventh stage (s7) of walking, the left leg may still be in the mid stance state, and the right leg may be in the mid swing (MSw) state. During transition from the sixth stage (s6) to the seventh stage (s7), the toes and heel of the left foot may all touch the ground, and the right leg may continuously perform the swing operation (s6 to s7).

In the eighth stage (s8) of walking, the left leg may be in the terminal stance (TSt) state, and the left leg may be in the initial swing (ISw) state. During transition from the seventh stage (s7) to the eighth stage (s8), the right foot may maintain a state of still not touching the ground, and the heel of the left foot may start to be separated from the ground (s7 to s8).

The above-described first to eighth stages (s1 to s8) may be continuously repeated during walking.

The detection unit 200 may detect information related to operations of at least one joint when transition (s8 to s1 and s7 to s8) of the walking stage during walking is performed. Signals generated in accordance with detection of the detection unit 200 may be transmitted to the processor 120, and/or temporarily or non-temporarily stored in a storage device, such as the memory, and then transmitted to the processor 120.

The processor 120 may output control signals to the joint driving unit 220 based on the information transmitted from the detection unit 200. For example, the processor 120 may determine operation states of the hip joint, the knee joint, and the ankle joint based on the information transmitted from the detection unit 200, and outputs control signals to the joint driving unit 220 to assist the determined operation states.

A torque may be generated in the joint driving unit 220 in accordance with the control signals, and each of joints 21, 31, and 41 may receive the corresponding torque to rotate the joints 21, 31 and 41.

The measuring unit 210 may measure information related to operations of the respective joints 21, 31, and 41 when the respective joints 21, 31, and 41 are rotated in accordance with control of the processor 120 in a case in which transition (s8 to s1 and s7 and s8) of the walking stage during walking is performed. The information measured in the measuring unit 210 may be transmitted to the processor 120, and/or temporarily or non-temporarily stored in a storage device and then transmitted to the processor 120.

For example, a rotation angle of the first joint 21 measured from the first measuring unit 210*a* may be transmitted to the processor 120.

The processor 120 may output the control signals to the holder driving unit 230 based on the information transmitted from the measuring unit 210.

Figure 6:
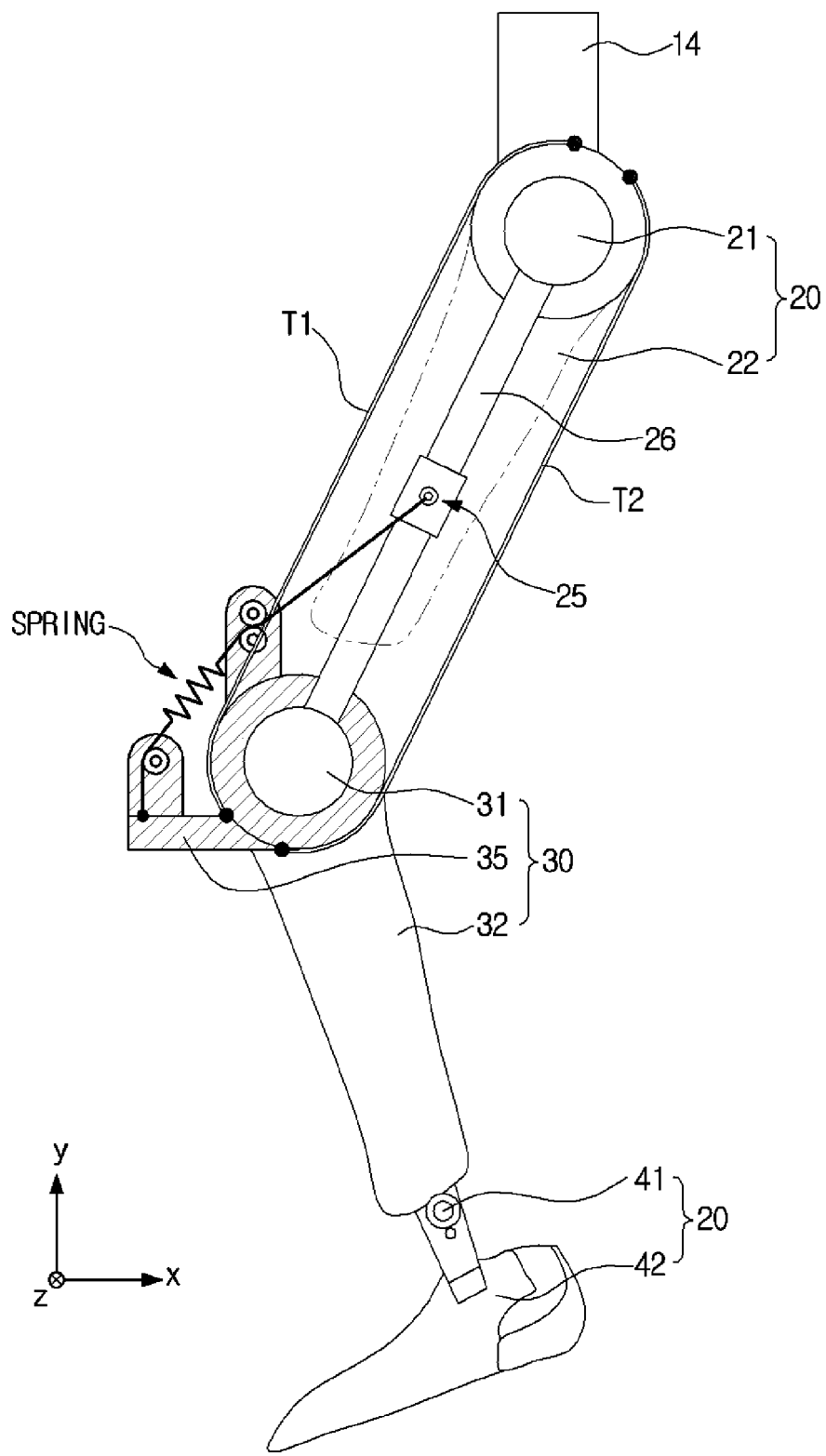
FIG. 6 is a view showing a structure of each of a first driving unit and a second driving unit according to some example embodiments.

For example, as discussed in more detail with regard to FIG. 6, in some example embodiments, in order to compensate for a weight of the wearer and a weight of the link, the processor 120 may output the control signals to the holder driving unit 220 based on the rotation angle transmitted from the first measuring unit 210*a*.

FIG. 6 is a view showing a structure of each of the first structure unit 20 and the second structure unit 30 according to some example embodiments.

Referring to FIG. 6, a fourth joint 35 may be provided at a periphery of the second joint 31. The fourth joint 35 may be an auxiliary joint that is separately rotatable without constraint on rotation of the second joint 31. The fourth joint 35 is connected with the first joint 21 by a first wire T1 and a second wire T2, and controlled by the first wire T1 and the second wire T2. In other words, the fourth joint 35 is rotatable independently from the second joint 31, but is controlled in such a manner that a reference axis of the fourth joint 35 maintains a parallel state on the x-y plane with the second waist support unit 14 that is a center axis of rotation of the first joint 21 by the first wire T1 and the second wire T2.

For example, a length of each of the first wire T1 and the second wire T2 which are wound around the first joint 21 and the fourth joint 35 may be changed in accordance with the rotation of the first joint 21. For example, when the first joint 21 is rotated in a front direction of the wearer, the length of the first wire T1 wound around the first joint 21 may increase and the length of the second wire T2 may be reduced, whereas the length of the first wire T1 wound around the fourth joint 35 is reduced and the length of the second wire T2 is increased.

In this manner, the lengths of the first wire T1 and the second wire T2 wound around the first joint 21 and the fourth joint 35 may change differently from each other, and therefore the reference axis of the fourth joint 35 may be controlled so as to maintain a parallel state on the x-y plane with the second waist support unit 14 that is a center axis of rotation of the first joint 21. That is, the fourth joint 35 is controlled so that the reference axis of the fourth joint 35 projected onto the x-y plane can achieve a vertical relationship with the ground, that is, a vertical relationship with the y axis.

A spring may be provided in the fourth joint 35, an end of the spring may be connected and fixed to the fourth joint 35, and the other end thereof may be movably connected to the first link 22 via the reference axis of the fourth joint 35. For example, a linear guide 26 may be provided in a longitudinal direction of the first link 22, and the other end of the spring is fixed to a spring holder 25.

The spring holder 25 may linearly move on the first link 22 through the linear guide 26. As the spring holder 25 is linearly moved, a length of the spring is increased or reduced, and therefore the walk-assistive apparatus 1 may obtain an elastic force by a spring constant.

The processor 120 may output the control signals to the holder driving unit 220 for movement of the spring holder 25.

The processor 120 may determine a movement position of the spring holder 25 based on the rotation angle transmitted from the first measuring unit 210*a*. Hereinafter, positioning of the spring holder 25 by the processor 120 will be described with reference to FIGS. 7 to 8A.

Figure 7:
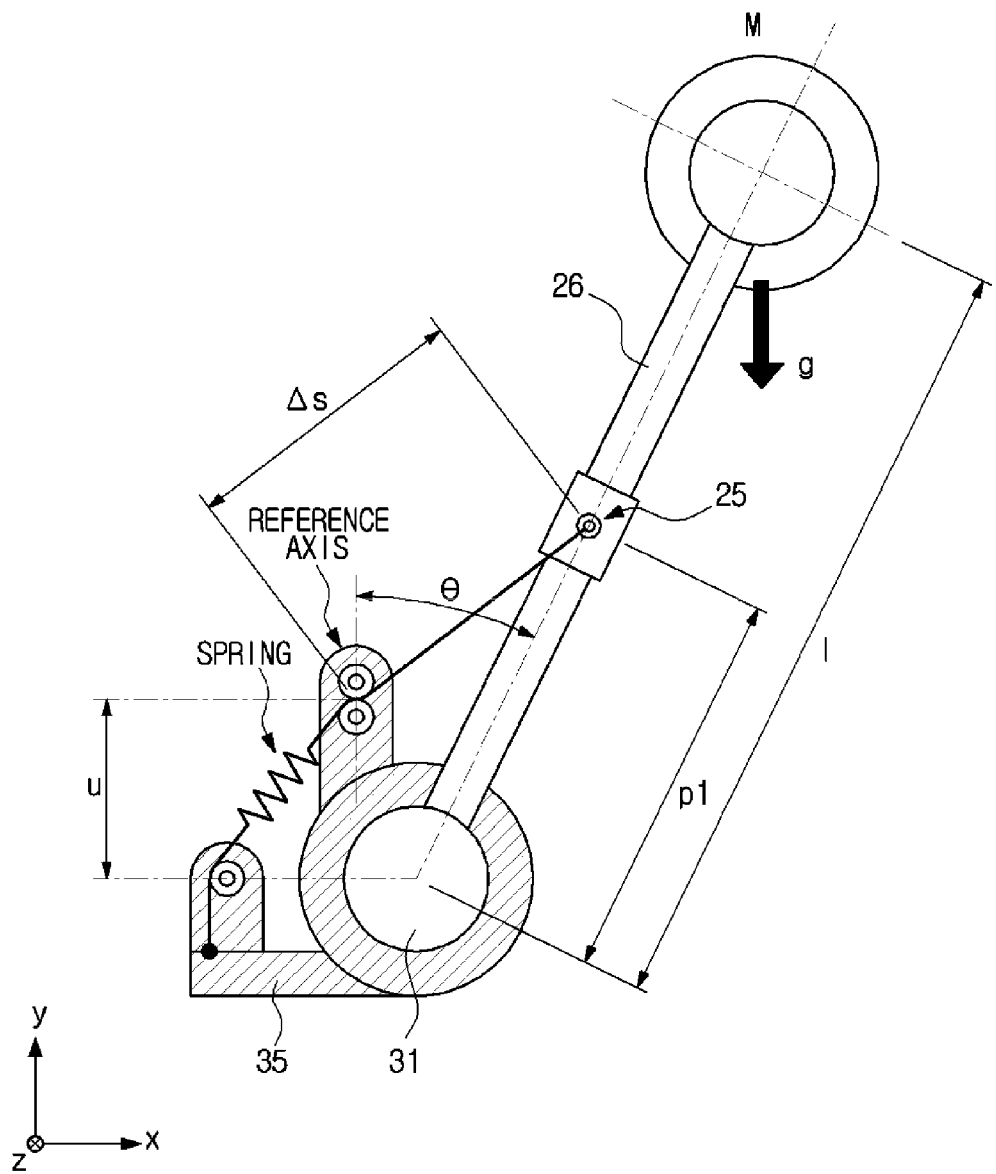
FIG. 7 is a view showing positioning when rotation is performed on a plane parallel with a gravity direction.

FIG. 7 is a view showing positioning when rotation is performed on a plane parallel with a gravity direction.

When the wearer lifts his or her toes, heel, and soles, for example, when the wearer walks while lifting the leg only in front and rear directions of the wearer, the first joint 21 may be rotated on a plane parallel with a gravity direction in accordance with the movement of the hip joint.

In FIG. 7, the plane parallel with the gravity direction is indicated as the x-y plane.

When it is assumed that the first link 22 forms an angle θ on the x-y plane with the second waist support unit 14 that is a center axis of the rotation of the first joint 21, the first link 22 may form the angle θ on the x-y plane with the reference axis of the fourth joint 35. As described above, this is because the reference axis of the fourth joint 35 maintains a parallel state on the x-y plane with the second waist support unit 14 that is the center axis of the rotation of the first joint 21. In this instance, θ may be defined as a rotation angle in a horizontal direction.

When it is assumed that M is a weight of the wearer including the weight of the walk-assistive apparatus 1, a torque (T) applied to the second joint to maintain the angle θ may be represented as the following Equation 1.

$$T = Mgl \cdot \sin(\theta) \qquad \text{[Equation 1]}$$

In Equation 1, M denotes a weight of the wearer including the weight of the walk-assistive apparatus, g denotes acceleration of gravity, l denotes a length of the first link, and θ denotes a rotation angle in a horizontal direction.

When the elastic force and the torque are kept in a static parallel state in order to replace the torque (T) with an elastic force by the spring, Equation 2 is obtained.

$$K \cdot \Delta s \cdot r = Mgl \cdot \sin(\theta),$$

where $$\tfrac{1}{2} r \cdot \Delta s = \tfrac{1}{2} u \cdot P_1 \cdot \sin(\theta) \qquad \text{[Equation 2]}$$

In Equation 2, K denotes a spring constant, Δs denotes a length of the spring connected to the reference axis of the fourth joint and the spring holder, r denotes a moment arm for the second joint by the spring, u denotes a distance between a position of the spring t and the center of the second joint on the reference axis of the fourth joint, and $P_1$ denotes a movement position of the spring holder from the center of the second joint.

The position $P_1$ of the spring holder 25 in Equation 2 may be determined in accordance Equation 3.

$$P_1 = \frac{Mgl}{K \cdot u} \qquad \text{[Equation 3]}$$

Specifically, when the first joint 21 and the first link 22 are rotated on a plane parallel with a gravity direction, the movement position of the spring holder 25 may be determined by M (weight of the wearer including the weight of the walk-assistive apparatus), g (acceleration of gravity), l (length of the first link), K (spring constant), and u (distance between the position of the spring and the center of the second joint on the reference axis of the fourth joint) regardless of the rotation angle θ in the horizontal direction.

As shown in Equation 3, when the movement position of the spring holder 25 is determined and the spring holder 25 is moved to the determined position, the torque (T) which should be applied to the second joint 31 in order to maintain the angle θ may not be required.

The torque (T) may not be required because by moving the spring and the spring holder 25, the weight in the horizontal direction may be compensated to maintain the rotation angle θ.

A case in which the wearer lifts his or her legs only in the front and rear directions has been described with reference to FIG. 7. However, the wearer may lift his legs in left and right directions during walking as well as in front and rear directions, and in this case, a method of determining the movement position of the spring holder 25 may be different.

Figure 8B:
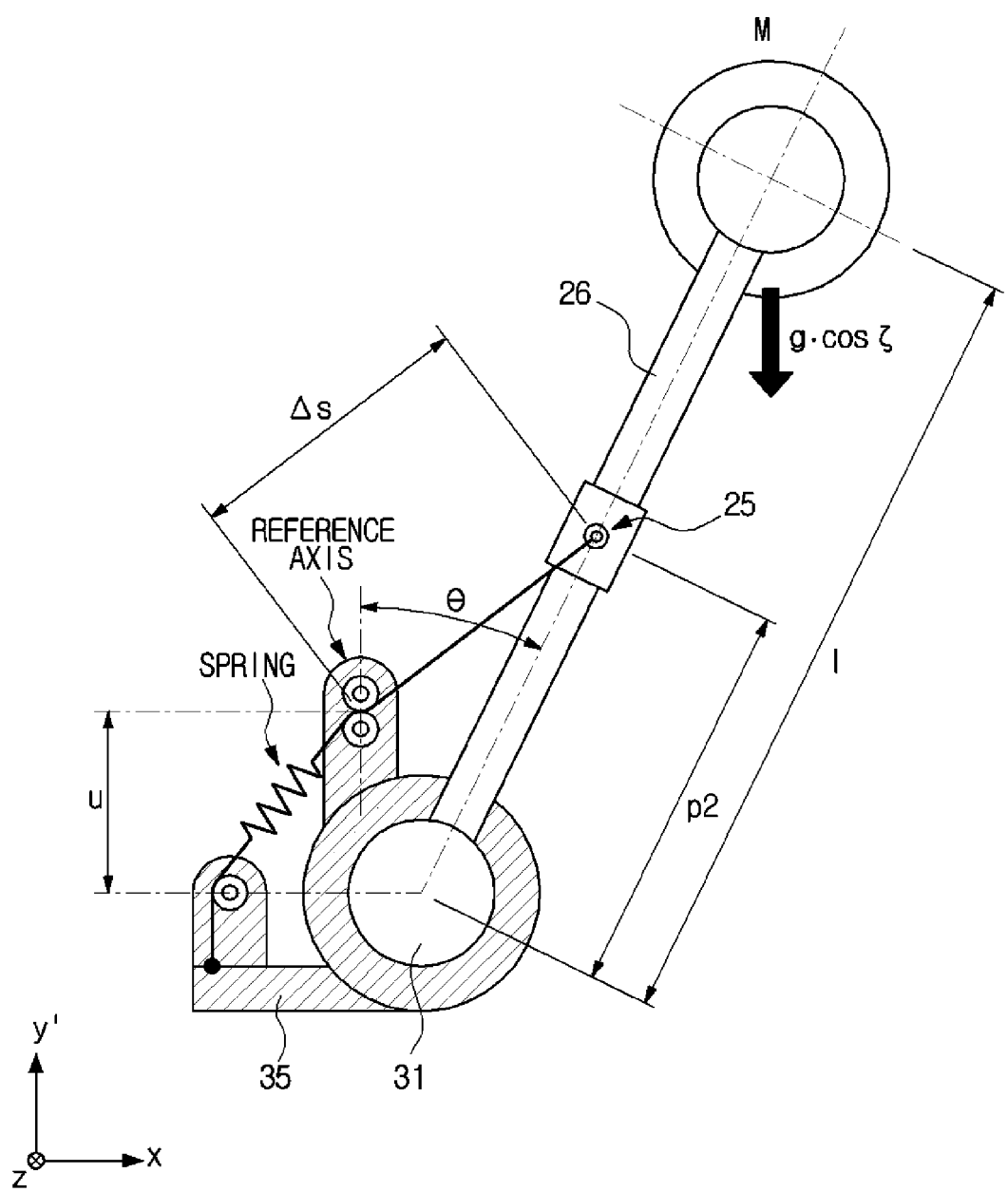

FIGS. 8A and 8B are views showing positioning when rotation is performed on a plane not parallel with a gravity direction.

Referring to FIGS. 8A and 8B, when the wearer walks while spreading his or her legs outwardly as well as lifting his or her legs in front and rear directions of the wearers, the first joint 21 may be rotated on a plane not parallel with the gravity direction in accordance with the movement of the hip joint. Although the plane not parallel with the gravity direction may continuously change in accordance with a spreading angle of the legs of the wearer, the plane on which the first joint 21 is rotated is fixed as an x-y' plane in FIGS. 8A and 8B for convenience of the description.

Specifically, when the wearer walks while spreading his legs outwardly by an angle ζ, the first joint 21 viewed from the front side or rear side (x axis) of the wearer forms an angle ζ with the second waist support unit 14 that is the center axis of the rotation of the first joint 21.

Thus, the first link 22 viewed from the front or rear side (x axis) of the wearer may form the angle ζ with the second waist support unit 14, that is, on the y axis and the y-z plane as shown in FIG. 8A. In other words, the first link 22 is rotated on a plane obtained by rotating the x-y plane with respect to the y axis by the angle ζ, and on a plane (hereinafter referred to as an x-y' plane) formed by the x axis and a y' axis. In this instance, ζ may be defined as a rotation angle in a vertical direction.

Thus, the first link 22 viewed from a direction perpendicular to the x-y' plane is the same as shown in FIG. 8B. The drawing of FIG. 8B is similar to the drawing of FIG. 7.

However, since the x-y' plane is obtained by rotating the x-y plane by ζ with respect to the y axis, acceleration for the mass M is changed to g·cos(ζ) in FIG. 8B.

Equation 3 may be modified to Equation 4 for determining a movement position $P_2$ of the spring holder 25.

$$P_2 = P_1 \cdot \cos(\zeta), \qquad \text{[Equation 4]}$$

where $$P_1 = \frac{Mgl}{K \cdot u}$$

In Equation 4, $P_1$ denotes a position from a center of the second joint 31 to the spring holder 25 at an initial ζ=0, M denotes a weight of the wearer including a weight of the walk-assistive apparatus, g denotes the acceleration of gravity, l denotes a length of the first link, K denotes a spring constant, and u denotes a distance between a position of the spring fixed to the reference bar of the fourth joint and the center of the second joint.

The processor 120 may determine the movement position $P_2$ of the spring holder 25 in accordance with Equation 4, based on the rotation angle ζ in the vertical direction transmitted from the first measuring unit 210a. The processor 120 may output control signals to the holder driving unit 220 so as to move the spring holder 25 to the determined position.

The movement of the spring holder 25 may be facilitated using a worm gear, and detailed description thereof will be made with reference to FIGS. 9A and 9B.

Figure 9A:
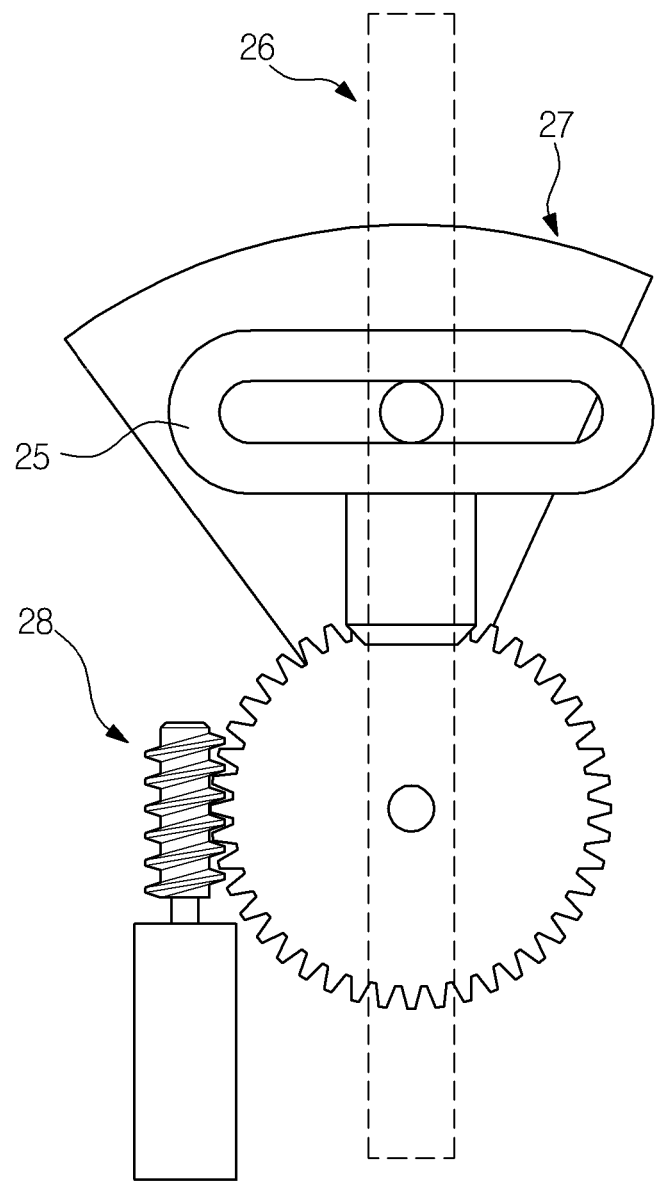
FIGS. 9A and 9B are views showing a structure of a spring holder and a peripheral structure of the spring holder.
Figure 9B:
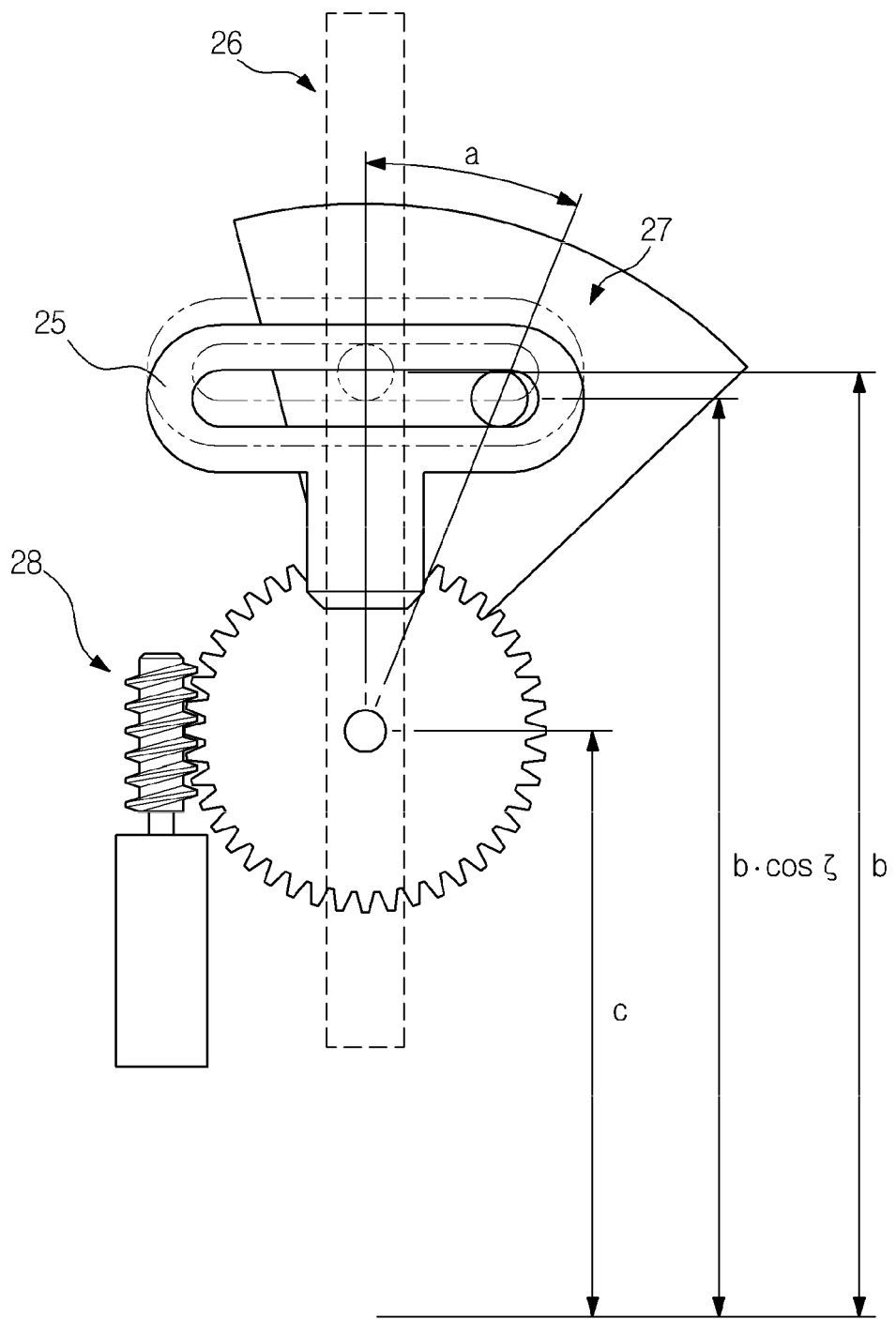

FIGS. 9A and 9B are views showing a structure of a spring holder and a peripheral structure of the spring holder.

Referring to FIGS. 9A and 9B, the spring holder 25 is linearly moved on the linear guide 26, and moved close to or away from the center of the second joint 31

The spring holder 25 includes a slot which penetrates the linear guide 26 in a vertical direction, and a position adjuster 27 for directly adjusting the movement position of the spring holder 25 using the slot and a worm gear 28 for adjusting rotation of the position adjuster 27 are provided in the periphery of the spring holder 25.

The position adjuster 27 may be divided into a first body formed into a fan shape and a second body formed into a gear shape, and the first body and the second body may be coupled. A portion which protrudes to be inserted into the slot of the spring holder 25, that is, a protrusion, is provided in the first body, and a bearing or a friction reducing member which is inserted into the slot to be smoothly moved inside the slot may be mounted outside of the protrusion.

The second body formed into the gear shape is engaged with the gap of the worm gear 28, and thereby is rotatable to the left and right in accordance with rotation of the worm gear 28.

The second body is rotated along with the rotation of the worm gear 28, and therefore the protrusion provided in the first body may be positioned at the center of the slot of the spring holder 25 as shown in FIG. 9A. The second body may be rotated to the right along with the rotation of the worm gear 28, and therefore the protrusion provided in the first body may be positioned at one end of the slot.

As can be seen from FIGS. 9A and 9B, when the protrusion is positioned at the center portion of the slot, a distance from the center of the second joint 31 to the spring holder 25, that is, the movement position of the spring holder 25, is the farthest from the second joint 31. Likewise, when the protrusion is moved to either ends of the slots, the movement position of the spring holder 25 gradually comes closer to the second joint 31. When the protrusion is positioned at the ends of the slots, the movement position of the spring holder 25 is the closest. That is, a position of the protrusion within the slot is adjusted by the rotation of the worm gear 28, and therefore the movement position of the spring holder 25 from the center of the second joint 31 may be adjusted.

Meanwhile, a method of obtaining an angle α at which the position adjuster 27 is rotated from the determined movement position P$_2$ of the spring holder 25 may be performed using Equation 5.

$$\alpha = \cos^{-1}\left(\frac{P_2 - C}{R}\right) = \cos^{-1}\left(\frac{P_1 \cdot \cos(\zeta) - C}{R}\right) \qquad \text{[Equation 5]}$$

In Equation 5, P$_2$ denotes a movement position of the spring holder 25 with respect to rotation ζ in the vertical direction, P$_1$ denotes a position to the spring holder 25 from the center of the second joint 31 at an initial ζ=0, C denotes a distance from the center of the second joint 31 to a rotation center of the position adjuster, and R denotes a distance from a rotation center of the position adjuster to a center of the protrusion.

When the spring holder 25 and the peripheral structure of the spring holder 25 are the same as above, the processor 120 calculates the rotation angle α of the position adjuster 27 using the determined movement position P$_2$ of the spring holder 25 and Equation 5.

The processor 120 calculates a rotating amount of the worm gear 28 corresponding to the calculated angle α using a gear ratio, and outputs control signals to the holder driving unit 230 so that the worm gear 28 is rotated by the calculated rotating amount. Thus, the position adjuster 27 is rotated by the angle α, and the spring holder 25 is moved to the determined position P$_2$.

The holder driving unit 230 may be implemented by a motor for generating a torque in accordance with electric energy supplied from a power source 110 or the like of the main body 10 in the same manner as in the joint driving unit 220, and the holder driving unit 230 may be implemented by at least one piston or cylinder device which is operated by the electric energy supplied from the main body 10 or the like or a pressure of a fluid, for example, by pressure such as oil pressure or air pressure to thereby generate a torque. The holder driving unit 230 may be implemented to include at least one motor or include at least one piston or cylinder device.

In FIGS. 9A and 9B, the movement of the spring holder 25 by the worm gear has been described, but example embodiments are not limited thereto.

As above, the components of the walk-assistive apparatus 1 and the operations of the components thereof have been described, and now a method of controlling the walk-assistive apparatus 1 will be described herein with reference to a given flowchart.

FIG. 10 is a flowchart showing a method of controlling a walk-assistive apparatus according to some example embodiments.

Referring to FIG. 10, in operation 500, the first measuring unit 210a may measure a rotation angle of the first joint 21.

The wearer may lift his or her legs in left and right directions of the wearer as well as in front and rear directions of the wearer while walking. In other words, the wearer may walk while spreading his or her legs outward as well as lifting his or her legs in the front and rear directions of the wearer. When the wearer walks while spreading his or her legs outward by an angle ζ, the first joint 21 may form an angle ζ on the y-z plane with the second waist support unit 14 being a center axis of the rotation of the first joint 21, that is, with the y axis. The first measuring unit 210a measures the rotation angle ζ in the vertical direction of the first joint 21.

In operation 510, the processor 120 may determine a position to which the spring holder 25 is to be moved using the measured rotation angle.

For example, based on the rotation angle ζ in the vertical direction measured by the first measuring unit 210a, the processor 120 may determine a movement position P$_2$ of the spring holder 25 using Equation 4 discussed above.

In operation 530, the processor 120 may instruct the holder driving unit 230 to move the spring holder 25 to the determined position.

For example when the movement of the spring holder 25 relies on the worm gear 28, the processor 120 may calculates a rotation angle α of the position adjuster 27 using the determined movement position P$_2$ of the spring holder 25 and Equation 5 discussed above.

The processor 120 may calculate a rotating amount of the worm gear 28 corresponding to the calculated angle α using the gear ratio, and output control signals to the holder driving unit 230 so that the worm gear 28 can be rotated by the calculated rotating amount. When the holder driving unit 230 is driven in accordance with the control signals, the position adjuster 27 is rotated by the angle α, and the spring holder 25 is moved to the determined position P$_2$.

As the spring holder 25 is moved, the length of the spring may be increased or reduced, an elastic force may be obtained in accordance with the change in the length of the spring, and a state of the wearer lifting his or her legs may be maintained or assisted through weight compensation by the elastic force. Thus, a separate torque applied to the walk-assistive apparatus 1 for maintaining and assisting the state of lifting the wearer's legs may not be required, and energy supplied from the power source 110 in order to apply the torque may be reduced.

As is apparent from the above description, the walk-assistive apparatus and the method of controlling the walk-assistive apparatus may use a mechanical element such as a spring to reduce energy, and weight compensation having uniform performance may be performed even in an arbitrary posture.

Although a few example embodiments have been shown and described, it would be appreciated by those skilled in the art that changes may be made in these example embodiments without departing from the principles and spirit of the example embodiments, the scope of which is defined in the claims and their equivalents.

What is claimed is:

1. A walk-assistive apparatus comprising:
   a walking assistance device including,
   at least one link connected to a joint, the at least one link configured to rotate in response to rotation of the joint;
   a spring having a first end and a second end, the first end of the spring connected to one or more of the link and the joint such that a length of the spring varies in accordance with the rotation of the link and the joint, and the second end connected to a spring holder; and a processor configured to control the length of the spring such that the spring compensates for variations in a gravitational weight when a wearer walks by,
    determining a movement position of the spring holder, and
    instructing a driver to move the spring holder to the movement position.

2. The walk-assistive apparatus according to claim 1, wherein
    the joint includes a first joint and a second joint respectively corresponding to a hip joint and a knee joint of the wearer, and
    the link includes a first link configured to connect the first joint and the second joint, and to rotate in response to rotation of the first joint.

3. The walk-assistive apparatus according to claim 2, wherein the joint includes an auxiliary joint provided at a periphery of the second joint such that the auxiliary joint is configured to rotate independently from the second joint.

4. The walk-assistive apparatus according to claim 3, further comprising:
    a reference bar that is connected to the auxiliary joint to form a reference axis of the rotation of the auxiliary joint.

5. The walk-assistive apparatus according to claim 4, wherein,
    the first end of the spring is connected to the auxiliary joint, and
    the second end of the spring is connected to the spring holder, the spring holder being movably provided on the first link.

6. The walk-assistive apparatus according to claim 5, wherein the processor is configured to control the length of the spring by moving the spring holder along the first link.

7. The walk-assistive apparatus according to claim 6, wherein the first joint is rotated in a front, rear, left, or right direction of the wearer in response to movement of the hip joint when the wearer walks.

8. The walk-assistive apparatus according to claim 7, wherein the processor is configured to rotate the auxiliary joint such that the reference bar maintains in a parallel state with a direction of the gravitational weight.

9. The walk-assistive apparatus according to claim 8, further comprising:
    at least one wire configured to connect the first joint and the auxiliary joint.

10. The walk-assistive apparatus according to claim 9, wherein
    the at least one wire is wound around the first joint and the auxiliary joint, and
    the processor is configured to adjust a length of the at least one wire such that the parallel state is maintained when the auxiliary joint is rotated.

11. The walk-assistive apparatus according to claim 8, wherein an intermediate portion of the spring between the first end and the second end is connected to the reference bar.

12. The walk-assistive apparatus according to claim 11, wherein
    the processor is configured to determine the movement position of the spring holder using:

$$P_2 = P_1 \cdot \cos(\zeta),$$

where $$P_1 = \frac{Mgl}{K \cdot u},$$

where $\zeta$ denotes an angle at which the first joint is rotated to a left or a right of the wearer in the direction of the gravitational weight as a center axis, $P_1$ denotes the movement position from a center of the second joint to the spring holder at an initial angle of the first joint $\zeta=0$, M denotes a weight of the wearer including a weight of the walk-assistive apparatus, g denotes an acceleration of gravity, l denotes a length of the first link, K denotes a spring constant, and u denotes a distance between a position of the spring connected to the reference bar and the center of the second joint.

13. The walk-assistive apparatus according to claim 6, further comprising:
    a worm gear, wherein
        the processor is configured to move the spring holder by driving the worm gear.

14. The walk-assistive apparatus according to claim 13, further comprising:
    a position adjuster configured to move the spring holder by rotating in accordance with driving of the worm gear.

15. The walk-assistive apparatus according to claim 14, wherein the spring holder includes a slot, and the position adjuster includes a protrusion, the protrusion configured to be inserted into the slot.

16. The walk-assistive apparatus according to claim 15, wherein the protrusion is configured to move inside the slot to move the spring holder when the position adjuster is rotated in accordance with the driving of the worm gear.

17. The walk-assistive apparatus according to claim 16, wherein
    the processor is configured to,
        determine a rotation angle $\alpha$ of the position adjuster using:

$$\alpha = \cos^{-1}\left(\frac{P_2 - C}{R}\right) = \cos^{-1}\left(\frac{P_1 \cdot \cos(\zeta) - C}{R}\right),$$

where $\zeta$ denotes an angle at which the first joint is rotated to a left or a right of the wearer in a direction of the gravitational weight as a central axis, $P_2$ denotes a determined movement position of the spring holder, $P_1$ denotes a position to the spring holder from a center of the second joint at an initial $\zeta=0$, denotes a distance from the center of the second joint to a rotation center of the position adjuster, and R denotes a distance from a rotation center of the position adjuster to a center of the protrusion, and
    controls the driving of the worm gear so that the position adjuster is rotated by the rotation angle $\alpha$.

18. A method of controlling a walk-assistive apparatus, the walk-assistive apparatus configured to be worn by a wearer, the method comprising:
    rotating a first joint in one or more of a front, rear, left, or right direction of the wearer in response to movement of a hip joint of the wearer when the wearer walks, the first joint connected via a first link to a second joint corresponding to a knee joint of the wearer;

measuring a rotation angle of the first joint;
determining a movement position of a spring holder on the first link in relation to the second joint based on the rotation angle; and
moving the spring holder to the movement position on the first link.

19. A walking assistance device comprising:
at least one link connected to a joint, the at least one link configured to rotate in response to rotation of the joint, the joint including a first joint, a second joint and an auxiliary joint, the first joint and the second joint respectively corresponding to a hip joint and a knee joint of a wearer, the auxiliary joint provided at a periphery of the second joint such that the auxiliary joint is configured to rotate independently from the second joint, and the link including a first link, the first link configured to connect the first joint and the second joint and to rotate in response to rotation of the first joint;
a spring connected to one or more of the link and the joint such that a length of the spring varies in accordance with the rotation of the link and the joint; and
a processor configured to control the length of the spring such that the spring compensates for variations in a gravitational weight when the wearer walks.

* * * * *